United States Patent

[19]

Schmidt

[11] 4,187,430

[45] Feb. 5, 1980

[54] TOMOGRAPH FOR THE PRODUCTION OF TRANSVERSE LAYER IMAGES

[75] Inventor: Martin Schmidt, Erlangen, Fed. Rep. of Germany

[73] Assignee: Siemens Aktiengesellschaft, Berlin & Munich, Fed. Rep. of Germany

[21] Appl. No.: 939,461

[22] Filed: Sep. 5, 1978

[30] Foreign Application Priority Data

Sep. 30, 1977 [DE] Fed. Rep. of Germany ...... 2744226

[51] Int. Cl.² ............................................. G03B 41/16
[52] U.S. Cl. ................................. 250/445 T; 250/360
[58] Field of Search ............................. 250/445, 360

[56] References Cited

U.S. PATENT DOCUMENTS 3,937,965  2/1976  Vasseur ........................... 250/445 T Primary Examiner—Craig E. Church Attorney, Agent, or Firm—Hill, Van Santen, Steadman, Chiara & Simpson

[57] ABSTRACT

A computer tomograph with a fan-shaped x-ray beam and two detector arrays. The two detector arrays are arranged in parallel and adjacent one another. Their lengths are dimensioned such that one detector array is suited for the head region, and the second, for the trunk (or body) region of the patient. The numbers of detectors of the detector arrays are equal, such that the division of the shorter detector array is finer than that of the longer one. There are connected, in parallel, to the input of the measured value converter two mutually corresponding detectors of the respective arrays. For each detector row, there is one light- and airproof chamber provided, and disposed between the two chambers and the two collimators there is a partition made of radiation-absorbing material.

1 Claim, 4 Drawing Figures

U.S. Patent     Feb. 5, 1980     4,187,430

TOMOGRAPH FOR THE PRODUCTION OF TRANSVERSE LAYER IMAGES

BACKGROUND OF THE INVENTION

The invention relates to a tomograph for the production of transverse layer images of a radiography subject with a radiation measuring arrangement comprising a radiation source which produces a fan-shaped beam of rays penetrating the radiography subject, the beam having a cross-sectional extent, perpendicular to the layer plane, equal to the layer thickness, and having an extent in the layer plane great enough for the entire radiography subject to be penetrated, and comprising also a radiation receiver which determines the radiation intensity behind the subject, with a rotating device for the measuring arrangement for irradiating the radiography subject from different directions, and with a measured value converter for transforming the signals delivered by the radiation receiver into a layer image, wherein the radiation receiver consists of a number of individual detectors, wherein the radiation receiver has two or more mutually parallel and adjacently arranged detector rows, each of which is assigned to a specific body region and each of which corresponds in its length to the body region assigned to it, the number of detectors per unit of length of a detector row being greater the shorter the detector row, wherein a control device is present for the radiation receiver which enables the selective detection of the x-ray beam by means of one detector row in each instance, and wherein there is arranged in front of each detector row one collimator each with laminae aligned with respect to the radiation source.

In this type of tomograph a short and a long detector row can be provided, for example, in which the numbers of detectors are the same. The short detector row can here serve the purpose of formation of an image of a cross section of the neck or head of a patient, and thus provides a good local resolution due to the finer division. The long detector row can serve the purpose of preparing transverse layer images in the region of a patient's trunk.

SUMMARY OF THE INVENTION

The object underlying the invention is to provide a tomograph of this type such that the output signals of the detectors exactly correspond to the received primary radiation; thus, that interfering influences due to atmospheric humidity fluctuations as well as due to scattered radiation are eliminated.

This object is achieved in accordance with the invention in that after the collimator, viewed in radiation direction, there is provided one lightproof and airtight chamber each for each detector row, and that there is arranged between the two chambers and the two collimators a partition of radiation-absorbing material. The atmospheric moisture conditions in the chambers are largely constant due to the tight seal of the chambers. To a great extent the partitions between the two chambers and the two collimators prevent a penetration of scattered radiation into the chamber housing the detector row used for measuring the primary radiation.

The invention is explained in more detail below with reference to an embodiment illustrated in the drawing; and other objects, features and advantages will be apparent from this detailed disclosure and from the appended claims.

DETAILED DESCRIPTION

Figure 1:
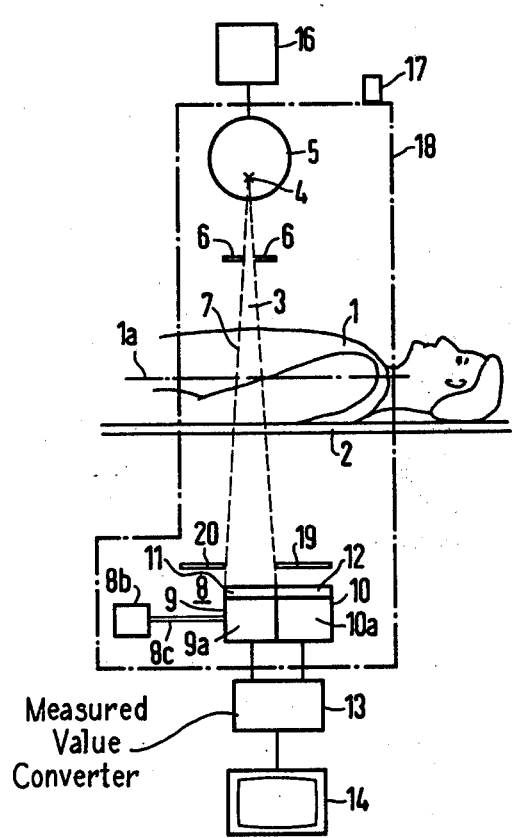
FIG. 1 illustrates an x-ray tomograph for the purpose of explaining the invention.

In the tomograph according to FIG. 1, a patient 1 is supported on a couch 2 and is irradiated by a fan-shaped x-ray beam 3. The beam 3 originates from the focus 4 of an x-ray tube 5 and is collimated by a primary ray diaphragm 6 in such a manner that its cross sectional extent perpendicular to the examined body layer 7 is equal to the layer thickness and that in the plane of the examined body layer 7 the extent of the beam is great enough so that the entire patient 1 is penetrated. A radiation receiver 8 is disposed after the patient, as viewed in the radiation direction, and consists of two mutually parallel and adjacently arranged detector rows 9 and 10. There is arranged in front of each of the detectors 9a, 9b, etc., and 10a, 10b, etc., of the detector rows 9 and 10, one collimator each. In FIG. 1, collimators 11 and 12 of detectors 9a and 10a are schematically illustrated.

In order to scan patient 1, e.g. the layer 7, the measuring arrangement 5, 8, is rotated about axis 1a through 360° around the patient. Scanning can proceed in such a manner that for instance the x-ray tube 5, which is fed by an x-ray generator 16, is pulsed once per angular degree, with the result that, in the case of e.g. 256 detectors per detector row, during one scan operation, 256×360 measuring signals are supplied to a measured value converter 13. The rotation proceeds by means of a rotation device 17 which rotates a frame 18 with the measuring arrangement 5, 8. The measured value converter 13 includes a computer which calculates an image of the irradiated body layer from the measured value signals. In order to reproduce this image, the measured value converter 13 is connected to a display unit 14.

The measuring signals during one rotation of measuring arrangement 5, 8, are delivered only from one of the detector rows 9 and 10, respectively. In the example, the detector row 9 delivers the measuring signals, while the detector row 10 is disposed behind a radiopaque diaphragm 19. If the detector row 10 is to be utilized for the production of the measuring signals, it is drawn into the x-ray beam 3 by means of a control device 8b, for example an electromagnet, via a rod 8c. The detector row 9 is then disposed behind a radiopaque diaphragm 20.

Figure 2:
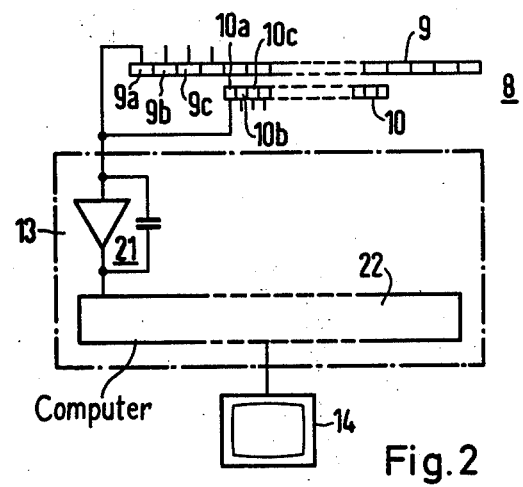
FIG. 2 illustrates the radiation receiver of the x-ray tomograph according to FIG. 1 in a view from above in conjunction with the associated measured value converter.

It is clear from FIG. 2 that the division of the detector row 10 is finer than the division of detector row 9. In the example, the number of detectors of each detector row 9, 10, is the same, and detectors of the detector rows 9, 10, corresponding to one another, respectively, are connected in parallel to an integrator of the measured value converter 13. In FIG. 2, this is illustrated only for detectors 9a and 10a. These detectors are connected to an integrator 21. In the example, there is assigned to each of the 256 input channels of a computer 22, one integrator to which two detectors are connected, respectively. The integrators hold the output signal of the respective detector for such a length of time until it has been taken over by computer 22, and they are then cleared. The interrogation of the output signals of the integrators proceeds by means of computer 22 in such a manner that the output signals of the integrators are read out in succession. Each input signal for an integrator originates only from one detector, respectively, since according to FIG. 1 only one detector row in each case detects and measures the x-radiation issuing from the patient 1.

Figure 3:
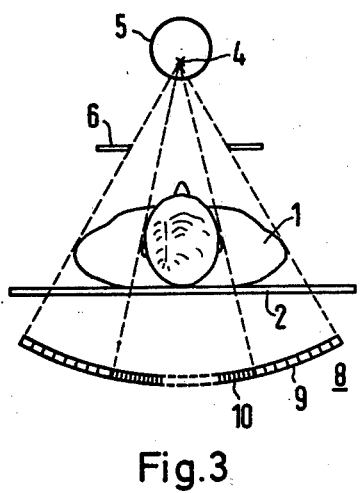
FIG. 3 illustrates a lateral view of the measuring arrangement in the tomograph according to FIG. 1.

From FIG. 3, it is clearly apparent that the lengths of the detector rows 9 and 10 correspond to the dimensions of the associated body regions. The detector row 9 is here assigned to the trunk of the patient 1, i.e. a relatively wide body layer, while the detector row 10 is assigned to the neck and head region of the patient 1, i.e. a comparatively narrow body layer.

From FIGS. 2 and 3, it is apparent that the number of detectors per unit of length of a detector row is greater the shorter the detector row. What is achieved thereby is that the local resolution, in the case of small examined body layers which are examined with the detector row 10, is greater than in the case of large examined body layers which are examined with detector row 9.

Figure 4:
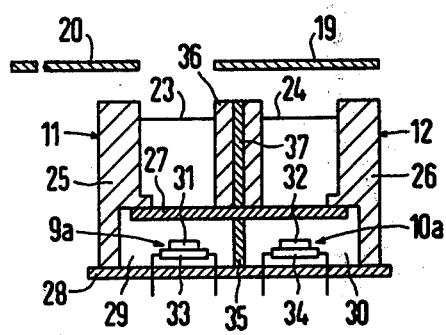
FIG. 4 is a cross sectional view showing the structure of the radiation receiver of the apparatus according to FIG. 1.

The section through the radiation receiver illustrated in FIG. 4 shows that the collimators 11 and 12 for each detector manifest a shaft or inlet passage which is defined by two laminae aligned to the x-ray tube 5. In FIG. 4, the two laminae 23 and 24 are visible. The lateral walls 25 and 26 of collimators 11 and 12, which can by way of example be made of steel, extend downwardly, and have a step on which a lightproof wall 27, pervious to x-rays, rests in a sealed fashion. A lightproof wall 28 lies airtight on the ends of the lateral walls 25 and 26.

The walls 25 through 28 define two light- and airtight chambers 29, 30, in which the two detector rows 9 and 10 are disposed. In FIG. 4, the detectors 9a and 10a are again illustrated. Each detector consists of a luminescent layer 31, 32 and a light sensitive diode 33, 34, whose connections are guided toward the exterior. Between chambers 29, 30, there is disposed a partition 35, impervious to x-rays, for instance a tantalum wall. The two collimators 11 and 12 are separated from one another by a steel wall 36 in the interior of which there is arranged a wall 37 similarly impervious to x-rays, made of radiation-absorbing material, e.g., tantalum.

In the illustrated position of the radiation receiver, walls 35 and 37 prevent scattered radiation from penetrating the wall 36 into chamber 30 and thus prevent scattered radiation from producing an undesired output signal at the detector 10a. Because of the light- and airproof arrangement, and the electrical shielding of the detector rows 9 and 10 in chambers 29, 30, the output signals of detectors 9a, 10a, etc., are largely independent of environmental influences.

It will be apparent that many modifications and variations may be effected without departing from the scope of the novel concepts and teachings of the present invention.

I claim as my invention:

1. A tomographic apparatus for the production of transverse layer images of a radiography subject with a radiation measuring arrangement comprising a radiation source which produces a fan-shaped beam of rays penetrating the radiography subject, whose cross-sectional extent, perpendicular to the layer plane, is equal to the layer thickness, and which is of sufficient extent in the layer plane that the entire radiography subject is penetrated, and comprising a radiation receiver which determines the radiation intensity behind the subject, a rotating device for the measuring arrangement for irradiating the radiography subject from different directions, and a measured value converter for the transformation of the signals delivered by the radiation receiver into a layer image, wherein the radiation receiver consists of a number of individual detectors, wherein the radiation receiver has two or more mutually parallel and adjacently arranged detector rows, each of which is assigned to a specific body region and corresponds in its length to the width of the body region assigned to it, wherein the number of detectors per unit of length of one detector row is greater the shorter the detector row, wherein a control device is present for the radiation receiver which renders possible the selective detection of the x-ray beam by one detector row in each case, and wherein one collimator with laminae aligned with respect to the radiation source is disposed before each detector series, characterized in that after each of the collimators (11, 12) for each of the detector rows (9, 10) as viewed in the radiation direction the radiation receiver has one light -and airtight chamber (29, 30) with a partition (35, 37) made of radiation-absorbing material between the chambers (29, 30) and the two collimators (11, 12).

* * * * *